(12) United States Patent
Copa et al.

(10) Patent No.: US 8,105,318 B2
(45) Date of Patent: Jan. 31, 2012

(54) INTRODUCER AND VALVE CAP FOR ANASTOMOSIS DEVICE

(75) Inventors: Vincent G. Copa, Minnetonka, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 629 days.

(21) Appl. No.: 11/939,908

(22) Filed: Nov. 14, 2007

(65) Prior Publication Data

US 2008/0114333 A1 May 15, 2008

Related U.S. Application Data

(60) Provisional application No. 60/865,728, filed on Nov. 14, 2006.

(51) Int. Cl.
*A61M 27/00* (2006.01)

(52) U.S. Cl. .......... 604/544; 604/540; 604/164.13; 604/166.01; 604/167.01; 604/192; 604/264; 604/270; 604/533; 604/536; 604/538

(58) Field of Classification Search .......... 604/544, 604/540, 164.13, 166.01, 167.01, 192, 264, 604/270, 533, 536, 538
See application file for complete search history.

(56) References Cited

U.S. PATENT DOCUMENTS

| | | | |
|---|---|---|---|
| 4,631,051 A * | 12/1986 | Harris | 604/9 |
| 5,007,897 A * | 4/1991 | Kalb et al. | 604/43 |
| 5,306,226 A * | 4/1994 | Salama | |
| 6,146,401 A * | 11/2000 | Yoon et al. | 606/192 |
| 6,599,311 B1 * | 7/2003 | Biggs et al. | |
| 7,918,831 B2 * | 4/2011 | House | 604/192 |
| 7,988,659 B2 * | 8/2011 | Shibata et al. | 604/43 |
| 2004/0087995 A1 * | 5/2004 | Copa et al. | 606/192 |
| 2004/0167547 A1 * | 8/2004 | Beane et al. | |
| 2005/0070938 A1 * | 3/2005 | Copa et al. | |
| 2005/0131431 A1 * | 6/2005 | Copa et al. | |
| 2006/0200178 A1 * | 9/2006 | Hamel et al. | |
| 2006/0206122 A1 * | 9/2006 | Copa et al. | |
| 2011/0082444 A1 * | 4/2011 | Mayback et al. | 604/544 |

FOREIGN PATENT DOCUMENTS

| | | | |
|---|---|---|---|
| EP | 1988000300851 | * | 2/1988 |
| WO | WO 96/16606 | * | 6/1996 |
| WO | WO 00/66199 | * | 11/2000 |
| WO | WO 01/36029 A1 * | | 5/2001 |
| WO | WO 2004/034913 | * | 4/2004 |

* cited by examiner

*Primary Examiner* — Tatyana Zalukaeva
*Assistant Examiner* — Ginger T Chapman
(74) *Attorney, Agent, or Firm* — Kimberly K. Baxter; Gregory L. Koeller

(57) ABSTRACT

Improved anastomosis devices having structural upgrades to increase ease of use while simultaneously increasing patent safety. The anastomosis device can include an introducer member having an introducer rod and an introducer cap to provide additional support to a catheter portion of the anastomosis device such that damage associated with installation of the catheter, deployment of tissue approximating structures and/or removal of the catheter can be minimized. The anastomosis device can further include a valve cap designed to constrain and reinforce a thin-walled section of a proximal funnel portion of the anastomosis device such that ballooning of the thin-walled section under the influence of a pressurized inflation fluid can be avoided during inflation as well as a time of tissue approximation and tissue healing.

6 Claims, 7 Drawing Sheets

INTRODUCER AND VALVE CAP FOR ANASTOMOSIS DEVICE

PRIORITY CLAIM

The present application claims priority to U.S. Provisional Application Ser. No. 60/865,728 filed Nov. 14, 2006 and entitled "INTRODUCER AND VALVE CAP FOR ANASTOMOSIS DEVICE", which is herein incorporated by reference in its entirety.

FIELD OF THE INVENTION

This application relates generally to anastomosis devices for approximating and joining tissue. More particularly, the present invention is directed to structural improvements to existing anastomosis devices so as to improve upon the introduction and operation of the anastomosis device during a medical procedure.

BACKGROUND OF THE INVENTION

Anastomosis devices and their associated procedures are generally used for connecting or re-connecting certain body tissues, e.g., as part of a surgical procedure. In typical situations, these tissues generally define a body lumen such as a blood vessel or intestinal, digestive or urinary tissue that has been severed and requires reconnection to complete a successful treatment.

Prior to the development and use of anastomosis devices, a surgeon generally performed delicate suturing operations with tiny, fine needles to reconnect these tissues. However, these suturing techniques to connect severed body lumens were a difficult and technique-sensitive task. One factor that especially made the suturing task difficult was that in joining these body lumens, there was often a very small or limited amount of tissue to work with, such as, for example, at the urethral stump and the bladder neck. In addition, tissue such as ureters, a proximal nerve bundle and sphincter, tend to be extremely sensitive. Due to these factors, the suturing technique requires extreme care to avoid complications such as leakage, difficulty in healing or failure to heal, or specific conditions such as incontinence or impotence.

In order to overcome the difficulties associated with conventional suturing techniques, anastomosis devices utilizing a variety of tissue approximating structures to maintain severed tissue in close approximating during healing have been developed. Representative anastomosis devices include those described in U.S. Patent Publications 2005/0070938A1, 2005/0131431A1, 2006/0200178A1 and 2006/0206122A1, which are herein incorporated by reference in their entirety and are commercially available from American Medical Systems of Minnetonka, Minn. These anastomosis devices advantageously use tissue approximating structures to reconnect severed tissues during anastomosis procedures, which can both reduce the risks during the surgical procedure and also provide a significant reduction in the amount of time required to perform certain anastomosis procedures. Because the anastomosis device will typically be surgically positioned within the patient for a significant period of time (e.g., while the healing process takes place), there is a need for the device to be sufficiently strong and flexible to accommodate the various stresses to which the device may be subjected while positioned within the patient.

One representative procedure utilizing these anastomosis devices can include a radical prostatectomy procedure in which, a surgeon removes all or most of a patient's prostate. The procedure generally leaves a severed urethral stump and a severed bladder neck, which must be reconnected so as to restore proper urinary functions. Through the use of a combination of retention features including an inflation balloon and a plurality of tissue approximating structures described as extendable tines, the urethral stump and bladder neck can be aligned and retained in approximation throughout a healing period for the tissue. While the urethral stump and bladder neck forcibly hold the tissue during healing, the anastomosis device provides a drainage lumen allowing bodily fluids and other materials to pass during the healing period.

While the aforementioned anastomosis device effectively reconnects tissue during certain surgical procedures, it would be advantageous to further improve upon the existing device to increase ease of use and increased patient safety.

SUMMARY OF THE INVENTION

The present application relates to structural improvements to anastomosis devices to make said anastomosis devices easier to use while simultaneously increasing patent safety. Generally, an anastomosis device of the present invention can comprise an introducer member having an introducer rod and an introducer cap to provide additional support to a catheter portion of the anastomosis device such that damage associated with installation of the catheter, deployment of tissue approximating structures and/or removal of the catheter can be minimized. The anastomosis device can further comprise a valve cap designed to interface with a proximal funnel portion of the anastomosis device such that ballooning of the proximal funnel portion can be avoided during inflation of an inflatable balloon proximate a distal end of the catheter portion.

In a first aspect, the present invention is directed to an anastomosis device having additional support structure within a catheter portion so as to minimize damage to the anastomosis device during insertion of the catheter portion, deployment of the retention members and/or removal of the catheter portion. The anastomosis device can comprise an introducer member having a flexible introducer rod and an introducer cap. The flexible introducer rod can be introduced into the catheter portion through an introduction port in a proximal funnel structure. The flexible introducer rod generally has a length sufficient such that when the introducer cap is positioned flush against the introduction port, a distal end of the flexible introducer rod is proximate a distal end of the catheter portion. With the introducer rod positioned within the catheter portion, support is provided to the catheter portion such that kinking of the catheter portion is avoided during insertion of the catheter portion. By eliminating potential kinks in the catheter portion, introduction of the catheter portion is enhanced and subsequent operation of retaining features and drainage lumen is enhanced. Once the catheter portion has been positioned as desired, a user can grasp the introducer cap and slidingly withdraw the introducer rod from the anastomosis device.

In another aspect, the present invention is directed to a method of positioning an anastomosis device to perform an anastomosis procedure. The method can comprise inserting an introducer rod within a port on a proximal funnel structure of an anastomosis device. The method can further comprise advancing the introducer rod into a catheter portion of the anastomosis device. The method further includes positioning the catheter portion a desired treatment location. The method further includes withdrawing the introducer rod from the anastomosis device once the catheter portion has been positioned relative to the treatment location.

In another aspect, the present invention is directed to an anastomosis device having a proximal funnel portion including a plurality of ports providing access to a catheter portion of the anastomosis device. One of the ports can comprise an inflation port fluidly interconnected to a distal inflation balloon located at a distal end of the catheter portion. An inflation lumen extends between the distal inflation balloon and an inflation valve at the inflation port. The inflation port can include a valve cap for placement over a thin-walled section of the proximal funnel portion where the inflation lumen fluidly connects the valve. By placing the valve cap of the thin-walled section, the valve cap provides structural reinforcement to the thin-walled section and prevents expansion and/or "ballooning" of the thin-walled section under the influence of pressurized fluid source used to inflate the distal inflation balloon. Reinforcement of the thin-walled section with the valve cap prevents structural failure of the proximal funnel portion such that the distal inflation balloon remains inflated throughout a tissue approximation and healing period that can last for at least one day and can extend into a number of weeks.

In another aspect, the present invention is directed to a method of maintaining inflation of a distal inflation balloon during a time of tissue approximation and healing. The method can comprise positioning a valve cap over a thin-section of an inflation port that is fluidly connected to a proximal funnel portion on an anastomosis device. The method can further comprise inflating the distal inflation balloon with a pressurized inflation balloon introduced through the inflation port. The method also includes preventing expansion and/or ballooning of the thin-walled section by constraining and reinforcing the thin-walled section with the inflation cap.

The above summary of the invention is not intended to describe each illustrated embodiment or every implementation of the present invention. The Figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
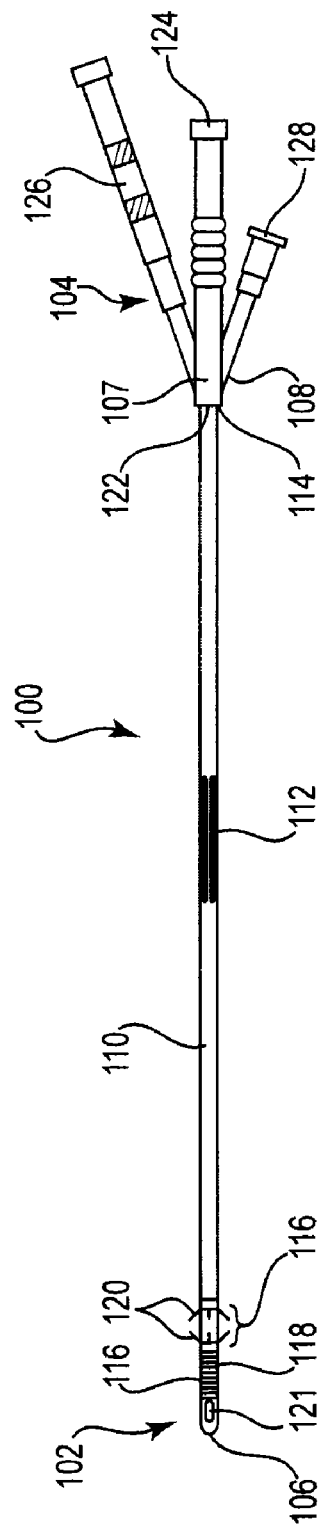
FIG. 1 is a plan view of a representative embodiment of an anastamosis device of the prior art.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Figure 2:
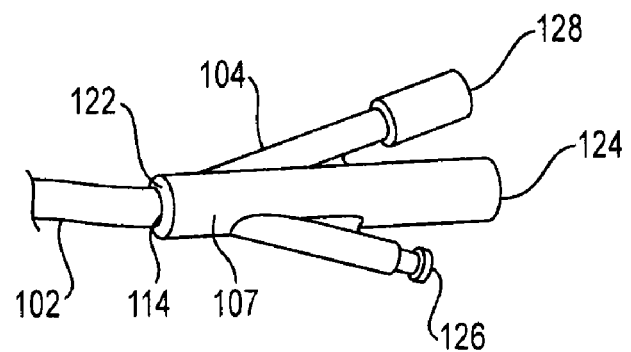
FIG. 2 is a perspective view of a proximal treatment end of the anastomosis device of FIG. 1.
Figure 3:
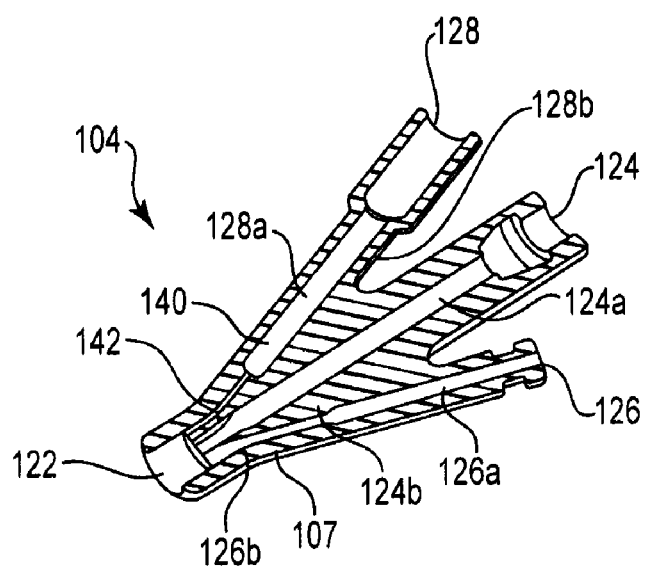
FIG. 3 is a perspective, section view of a funnel portion of the anastomosis device of FIG. 1.

As illustrated in FIGS. 1, 2 and 3, an anastomosis device 100 of the prior art generally comprises a catheter portion 102 and a funnel portion 104 between a distal treatment end 106 and a proximal control end 108. Catheter portion 102 generally comprises a tubular body 110 defining an interior lumen 112 between the distal treatment end 106 and a proximal connection end 114. At the distal treatment end 106, catheter portion 102 can comprise a variety of retention elements 116 such as, for example, a distal inflation balloon 118 and one or more sets of distal tines 120 as well as a drainage aperture 121. Though not illustrated, it will be understood that interior lumen 112 provides space for connecting an inflation tube between the distal inflation balloon 118 and the funnel portion 104 as well as one or more guidewires for connecting the distal tines 120 with the funnel portion 104 as well as connecting a drainage lumen between the drainage aperture 121 and funnel portion 104.

Funnel portion 104 generally comprises a funnel body 107 having a catheter receiving aperture 122 and a plurality of connecting ports including a drainage port 124, a control port 126 and an inflation port 128. Drainage port 124, control port 126 and inflation port 128 include a corresponding port lumen, i.e., a drainage lumen 124a, a control lumen 126a and an inflation lumen 128 operably connected to the catheter receiving aperture 122. Proximal connection end 114 is inserted into catheter receiving aperture 122 so as to operably interconnect the funnel portion 104 with the catheter portion 102.

Figure 4:
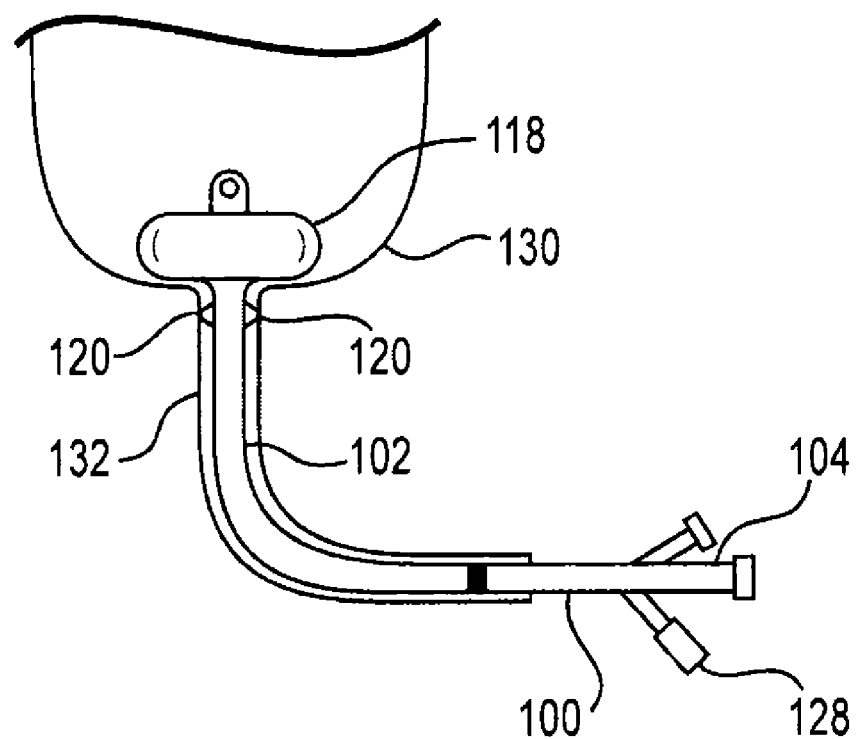
FIG. 4 is an illustration of an anastomosis procedure performed with the anastomosis device of FIG. 1.

Referring to FIG. 4, the use of anastomosis device 100 is illustrated generally with respect to connection of a patient's bladder 130 with a patient's urethra 132 such as, for example, during a radical prostatectomy. Generally, distal treatment end 106 is inserted into a urethral opening 134, through the urethra 132 and into the bladder 130. At this point, a pressurized inflation fluid can be introduced through the inflation port 128 to inflate the distal inflation balloon 118. With the distal inflation balloon 118 inflated, the bladder 130 can be pulled into approximation with the separated urethra 132 such that the distal tines 120 can be deployed to grasp and retain the bladder 130 and urethra 132 in close approximation during a healing period.

Figure 5:
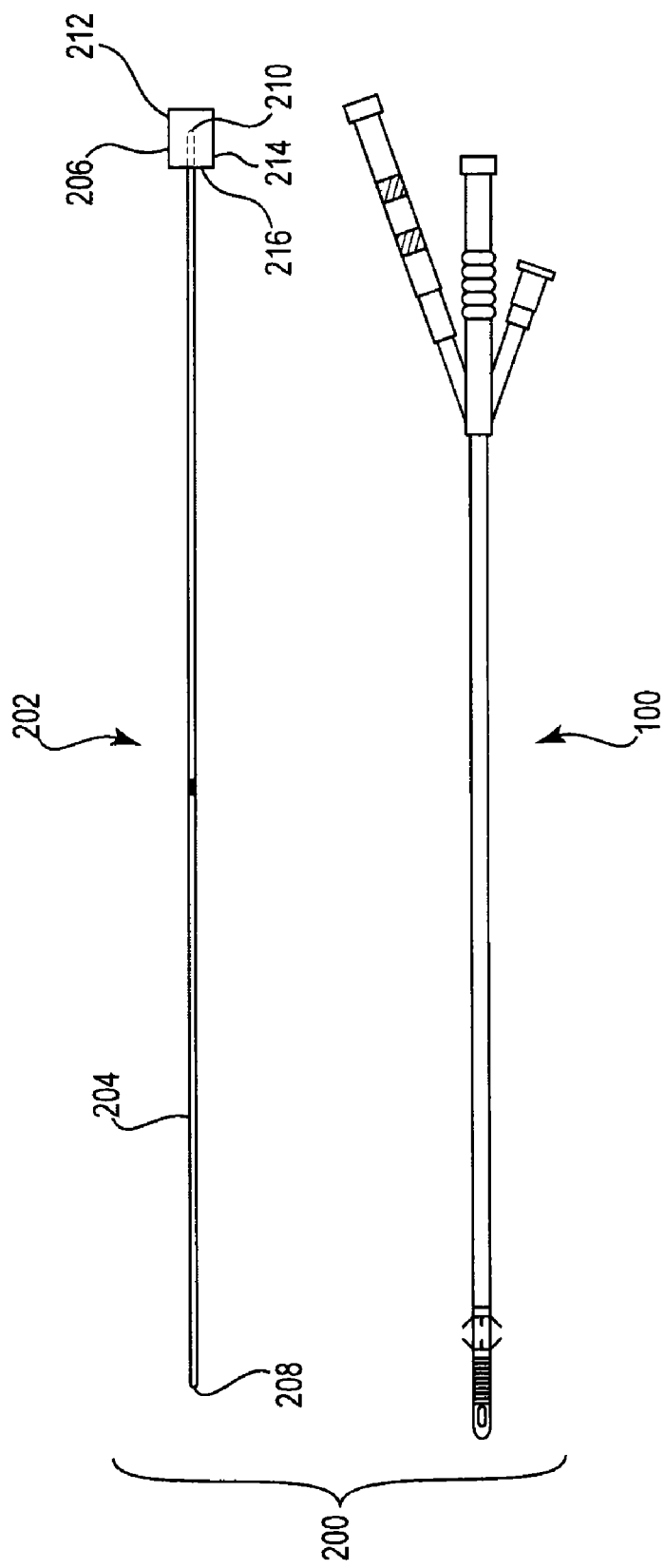
FIG. 5 is a plan view of an anastomosis system according to an embodiment of the present invention.

Referring now to FIG. 5, an embodiment of an improved anastomosis system 200 can comprise anastomosis device 100 and an introducer assembly 202. Introducer assembly 202 generally comprises an elongated insertion rod 204 and an insertion cap 206. Insertion rod 204 generally comprises a solid, flexible rod made from suitable materials including medical grade plastics or nitinol. Preferably insertion rod 204 includes a distal rounded tip 208 and a proximal connecting end 210. Insertion cap 206 generally comprises a cap body 212 defining a grip perimeter 214 and a flanged insertion surface 216. Cap body 212 can comprise suitable materials such as, for example, a moldable plastic such that cap body 212 can be molded over proximal connecting end 210 to operably connect the insertion rod 204 and insertion cap 206.

Figure 6:
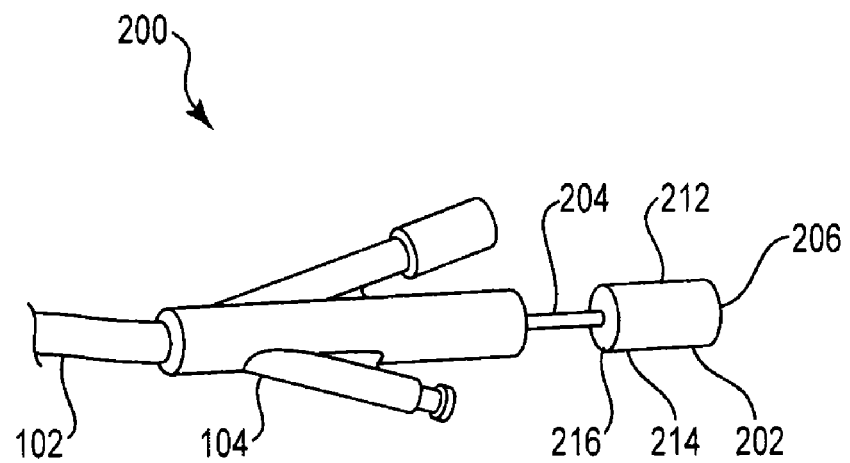
FIG. 6 is a perspective view of a proximal treatment end of the anastamosis system of FIG. 5.
Figure 7:
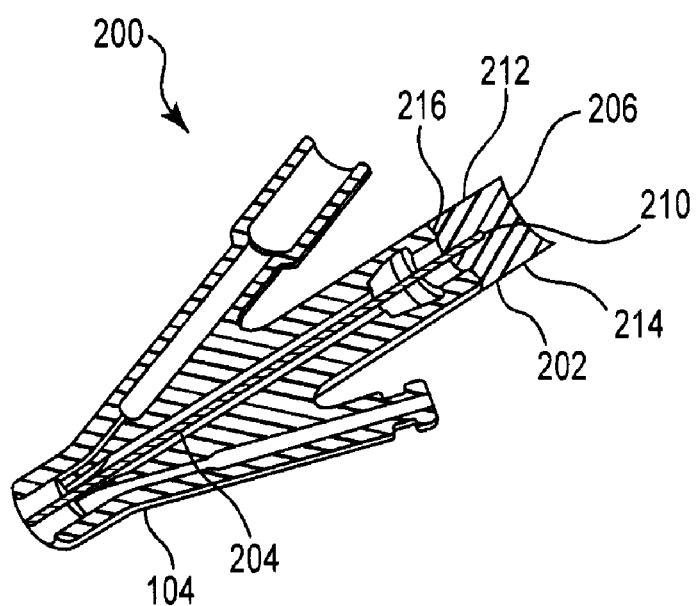
FIG. 7 is a perspective, section view of a proximal treatment end of the anastomosis system of FIG. 5.

Prior to utilizing anastomosis system 200 in an anastomosis procedure, introducer assembly 202 is operably inserted into anastomosis device 100 as illustrated in FIGS. 6 and 7. Generally, insertion rod 204 is positioned such that distal rounded tip 208 is inserted into drainage port 124. By holding the grip perimeter 214, a medical professional continues advancing the insertion rod 204 into the drainage port 124 until flanged insertion surface 216 contacts the drainage port 124 preventing further advancement of the insertion rod 204.

With the flanged insertion surface 216 flush against the drainage port 124, the distal rounded tip 208 is located proximate the distal treatment end 106.

With anastomosis system 200 fully assembled, the catheter portion 102 can be positioned within a lumen in the patient such as the urinary tract as illustrated and described with respect to FIG. 4. Insertion rod 204 provides internal support during insertion of the catheter portion 102 such that as the insertion rod 204 navigates the twisting contours of the patient's lumen, tubular body 110 cannot be fully crimped or kinked. The solid nature of insertion rod 204 prevents full compression of the tubular body 110 which can damage or otherwise restrict the operational nature of components, such as an inflation lumen, drainage lumen or guidewires, within interior lumen 112. Once the catheter portion 102 has been positioned within the patient lumen as desired by the medical professional, the introducer assembly 202 can be removed by again grasping the grip perimeter 214 and withdrawing the insertion rod 204 from the catheter portion 102 and ultimately, the funnel portion 104. Once the introducer assembly 202 has been withdrawn from the anastomosis device 100, an external drainage lumen can be connected to the drainage port 124.

Referring again to FIGS. 1, 2 and 3, funnel portion 104 generally comprises thin walled sections at the junction of the various ports with the catheter receiving aperture 122. These thin-walled sections include a drainage wall section 124b, a control wall section 126b and an inflation wall section 128b. The thin wall sections at drainage wall section 124b and control wall section 126b generally have no deleterious effect on the operation of anastomosis device 100 as the drainage lumen and guidewires passing through these section provide little if no operational stress on these sections. Conversely, inflation wall section 128b is subjected to increased pressures during operation as a pressurized inflation fluid is introduced into the inflation port 128, whereby the pressurized inflation fluid is collected in a fluid chamber 140 prior to entering an inflation fluid lumen 142 which extends through the interior lumen 112 and operably connects to the distal inflation balloon 118.

Figure 8:
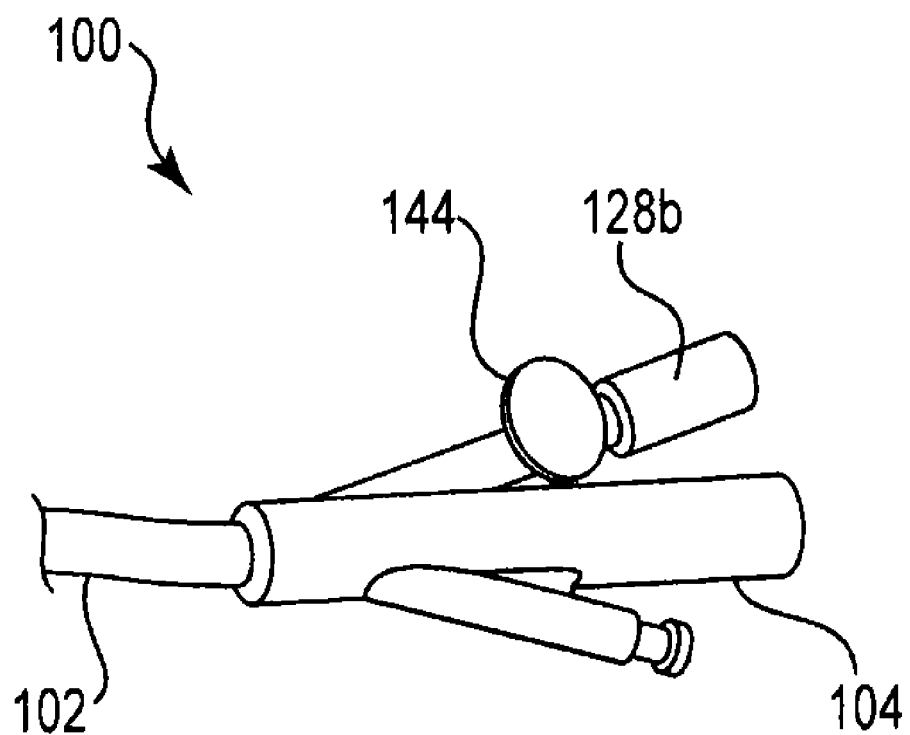
FIG. 8 is a perspective view of a proximal treatment end of the anastomosis device of FIG. 1 including a thin walled inflation section ballooned under pressure to an expanded disposition.

With the distal inflation balloon 118 inflated such as, for example, as shown in FIG. 4, the fluid chamber 140 is continually exposed to pressure pushing outward against the inflation wall section 128b. As illustrated in FIG. 8, the pressure applied to the thin walled section at inflation wall section 128b can cause expansion or "ballooning" of the inflation wall section 128b wherein it assumes an expanded disposition 144. While expanded disposition 142 can allow the distal inflation balloon 118 to remain inflated, the potential for potential piercing or bursting of the inflation wall section 128b is substantially increased, which can lead to the rapid deflation of distal inflation balloon 118. With distal inflation balloon 118, the potential exists for damage to the lumen in which the anastomosis device resides.

Figure 9:
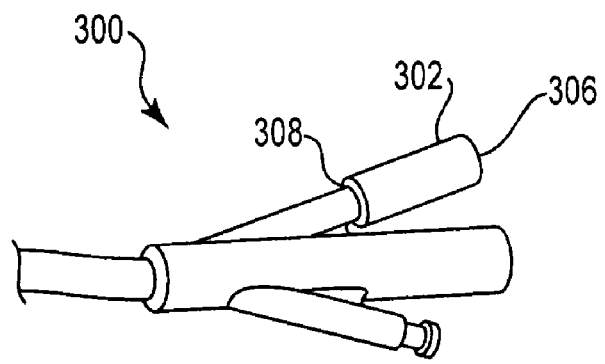
FIG. 9 is a perspective view of a proximal treatment end of an embodiment of an anastomosis device having an improved funnel portion according to the present invention.
Figure 10:
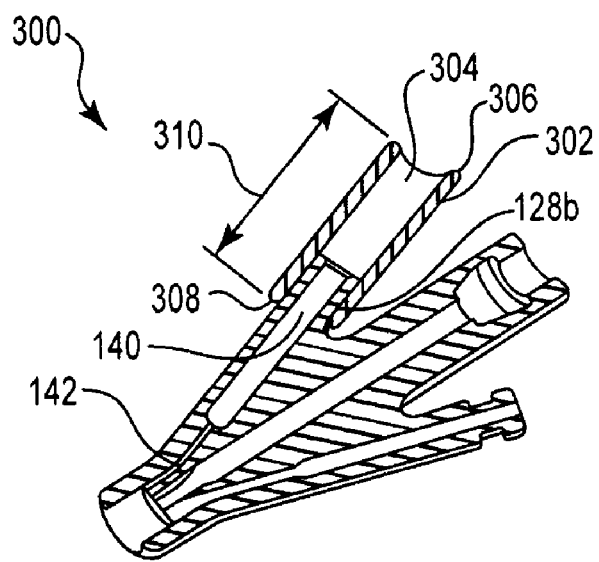
FIG. 10 is a section view of the improved funnel portion of the anastomosis device of FIG. 9.

Referring now to FIGS. 9 and 10, an improved funnel portion 300 can substantially resemble the configuration of funnel portion 104 with the further inclusion of a protective inflation cap 302. Protective inflation cap 302 generally has a cap lumen 304 defined between a first cap end 306 and a second cap end 308. A cap length 310 is generally defined between the first cap end 306 and the second cap end 310.

Generally, the cap lumen 304 is slightly larger than the inflation port 128 such that a press fit operation can be utilized to couple the protective inflation cap 302 to the inflation port 128. Cap length 310 is generally of a sufficient length such that the protection inflation cap 302 slides over and covers the inflation wall section 128b. When positioned over the inflation wall section 128b, the protective inflation cap 302 constrains and reinforces the inflation wall section 128b such that pressurized fluid within the fluid chamber 140 cannot expand or balloon the inflation wall section 128b to expanded disposition 142. As such, the placement of protective inflation cap 302 over the inflation wall section 128b insures the distal inflation balloon 118 remains inflated throughout a desired healing period and is only deflated by an intentional action of the medical professional.

Although specific individual examples have been illustrated and described herein, it will be appreciated by those of ordinary skill in the art that the introducer assembly 202 and improved funnel portion 300 can be used either individually or in combination to improve upon current anastomosis device designs. In addition, this application is intended to cover further adaptations or variations of the inventive subject matter disclosed herein. Therefore, it is intended that the invention be defined by the attached claims and their legal equivalents.

The invention claimed is:

1. An anastomosis system comprising:
an anastomosis device having a distal treatment end and a proximal connection end, the anastomosis device having a catheter portion and a funnel portion, the funnel portion including access ports in fluid connection to a catheter receiving aperture for attaching to the catheter portion, the access ports including a drainage port, a control port and an inflation port; and
a removable introducer assembly having a flexible insertion rod and an insertion cap, the flexible insertion rod having a connecting end attached to the insertion cap and a distal tip, the insertion cap defining a grip perimeter and a flanged insertion surface wherein the flexible insertion rod is insertable into the drainage port such that the flexible insertion rod traverses the catheter portion until the flanged insertion surface abuts the drainage port such that the distal tip resides at the distal treatment end, whereupon following positioning of the distal treatment end, the removable introducer assembly is removed from the anastomosis device by gripping the insertion cap and withdrawing the flexible insertion rod from the catheter portion and the funnel portion.

2. The anastomosis system of claim 1, wherein the flexible insertion rod comprises a solid cross-section.

3. The anastomosis system of claim 2, wherein the solid cross-section of the flexible insertion rod prevents kinking or collapsing of the catheter portion during insertion of the catheter portion into a body lumen.

4. The anastomosis system of claim 1, wherein the distal tip comprises a round tip.

5. An anastomosis system comprising:
an anastomosis device having a distal treatment end and a proximal connection end, the anastomosis device having a catheter portion and a funnel portion, the funnel portion including access ports in fluid connection to a catheter receiving aperture for attaching to the catheter portion, the access ports including a drainage port, a control port and an inflation port, wherein the drainage port is defined by a thin-walled section defining an interior inflation fluid chamber; and
a protective inflation cap having a cap lumen defined between a first cap end and a second cap end, the cap lumen being sized for placement over the thin-walled section to constrain the thin-walled section from expansion under the influence of a pressurized inflation fluid within the interior inflation fluid chamber.

6. The anastomosis system of claim 5, wherein a cap length is defined between the first cap end and the second cap end such that the cap length is sufficient to allow for placement of the protective inflation cap over the thin-walled section defining the interior fluid chamber.

* * * * *